(12) United States Patent
Kearney et al.

(10) Patent No.: US 11,058,891 B2
(45) Date of Patent: Jul. 13, 2021

(54) SYSTEMS AND METHODS FOR CLOUD-BASED RADIATION THERAPY TREATMENT PLANNING

(71) Applicant: Board of Regents, The University of Texas System, Austin, TX (US)

(72) Inventors: Vasant P. Kearney, San Francisco, CA (US); Ko-ay Timmy Siauw, Berkeley, CA (US); Xun Jia, Dallas, TX (US); Steve Bin Jiang, Southlake, TX (US); Xuejun Gu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 662 days.

(21) Appl. No.: 15/359,415

(22) Filed: Nov. 22, 2016

(65) Prior Publication Data

US 2017/0143994 A1    May 25, 2017

Related U.S. Application Data

(60) Provisional application No. 62/259,007, filed on Nov. 23, 2015.

(51) Int. Cl.
| | |
|---|---|
| *G06F 19/00* | (2018.01) |
| *A61N 5/10* | (2006.01) |
| *H04L 29/08* | (2006.01) |
| *G16H 20/40* | (2018.01) |
| *G16H 70/60* | (2018.01) |
| *G16H 30/40* | (2018.01) |

(52) U.S. Cl.
CPC .............. *A61N 5/103* (2013.01); *G16H 20/40* (2018.01); *G16H 30/40* (2018.01); *G16H 70/60* (2018.01); *H04L 67/10* (2013.01); *H04L 67/12* (2013.01)

(58) Field of Classification Search
CPC .................. A61N 5/103; A61N 5/1031; A61N 5/1037–1039; A61N 2005/1041
See application file for complete search history.

(56) References Cited

U.S. PATENT DOCUMENTS

| | | | |
|---|---|---|---|
| 8,693,744 B2 | 4/2014 | Piper | |
| 8,805,035 B2 | 8/2014 | Piper | |
| 8,908,940 B1 | 12/2014 | Piper | |
| 2008/0253518 A1* | 10/2008 | Foshee | ................... A61N 5/103 378/65 |

(Continued)

OTHER PUBLICATIONS

Welcome to MIMCloud; https://mim-cloud.appspot.com; Nov. 17, 2015.

(Continued)

*Primary Examiner* — Carrie R Dorna
(74) *Attorney, Agent, or Firm* — Thomas|Horstemeyer LLP

(57) ABSTRACT

A cloud-based radiation therapy treatment planning system (TPS). The TPS changes the clinical workflow of the radiotherapy treatment planning process, by increasing the mobility and computational power of the treatment planning software and hardware architecture. The system is divided into computational components. A user device includes a light and flexible user interface, while the server side entails a hospital relay server, and/or a graphics processing unit cluster server. The TPS computational architecture enables the computational power of a GPU-cluster server on a tablet, laptop, or smartphone.

26 Claims, 11 Drawing Sheets

(56) References Cited

U.S. PATENT DOCUMENTS

| | | | | |
|---|---|---|---|---|
| 2010/0081971 | A1* | 4/2010 | Allison | A61F 7/00 601/2 |
| 2014/0350863 | A1* | 11/2014 | Hartman | A61N 5/1031 702/19 |
| 2016/0213947 | A1* | 7/2016 | Han | G06T 7/246 |
| 2016/0228728 | A1* | 8/2016 | Dempsey | A61N 5/1049 |

OTHER PUBLICATIONS

Ananthanarayanan, S. "Use of of ultrabook and iPad mini for processing, display, storage, and transmission of medical images using MIM software", Journal of Medical Physics, Jan.-Mar. 2014, 39(1)-56-59.

Schenkan, et al., "Inexpensive solutions to enhance remote cancer care in community hospitals", UMPC McKeesport Hospital, PA., Community Oncology, Nov. 2013.

Kawashiro, et al., "Experience of a Videoconference System with Medical Information Desktop Sharing for Radiation Therapy and Evaluation of its Usefulness", Dept of Radiation Oncology; Scientific Research; International Journal of Medical Physics, Clinical Engineering and Radiation Oncology, 2014.

Kouloulias, et al. "A scenario for web-based radiation treatment planning structure: a new tool for quality assurance procedure?" Technology and health care; official journal of the European society for engineering and medicine, Feb. 2003.

Shen, et al., "MIAPS: A web-based system for remotely accessing and presenting medical images", Computer Methods and Programs in Biomedicine, 113, 2014.

Na, et al. "Toward a web-based real-time radiation treatment planning system in a cloud computing environment". IOP Publishing, Physics in Medicine and Biology, 2013.

Jeleén U, Söhn M, Alber M. A finite size pencil beam for IMRT dose optimization. Physics in medicine and biology. 2005;50(8):1747.

Aspradakis MM, Morrison Rh, Richmond Nd, Steele A. Experimental verification of convolution/superposition photon dose calculations for radiotherapy treatment planning. Physics in medicine and biology. 2003;48(17):2873.

Ma C, Li J, Pawlicki T, Jiang S, Deng J, Lee M, et al. A Monte Carlo dose calculation tool for radiotherapy treatment planning. Physics in medicine and biology. 2002;47(10):1671.

Wu Q, Mohan R. Algorithms and functionality of an intensity modulated radiotherapy optimization system. Medical physics. 2000;27(4):701-11.

Webb S. The physical basis of IMRT and inverse planning. The British Journal of Radiology. 2014.

Shepard D, Earl M, Li X, Naqvi S, Yu C. Direct aperture optimization: a turnkey solution for step-and-shoot IMRT. Medical physics. 2002;29(6):1007-18.

Miles EA, Clark CH, Urbano MTG, Bidmead M, Dearnaley DP, Harrington KJ, et al. The impact of introducing intensity modulated radiotherapy into routine clinical practice. Radiotherapy and oncology. 2005;77(3):241-6.

Craft D, McQuaid D, Wala J, Chen W, Salari E, Bortfeld T. Multicriteria VMAT optimization. Medical physics. 2012;39(:2):686-96.

Jia X, Ziegenhein P, Jiang SB. GPU-based high-performance computing for radiation therapy. Physics in medicine and biology. 2014;59(4):R151.

Chai X, Liu L, Xing L. SU-D-BRD-02: A Web-Based Image Processing and Plan Evaluation Platform (WIPPEP) for Future Cloud-Based Radiotherapy, Medical Physics. 2014;41(6):113.

Suzuki K, Hirasawa Y, Yaegashi Y, Miyamoto H, Shirato H. A web-based remote radiation treatment planning system using the remote desktop function of a computer operating system: a preliminary report. Journal of telemedicine and telecare. 2009;15(8):414-8.

Hou, et al., A cloud gaming system based on NVIDIA Grid GPU. 2014 13th International Symposium on Distributed Computing and Applications to Business, Engineering and Science.

Securing Medical Imaging in the Cloud, A Whitepaper by DICOM Grid, Dec. 21, 2015.

* cited by examiner

SYSTEMS AND METHODS FOR CLOUD-BASED RADIATION THERAPY TREATMENT PLANNING

CROSS-REFERENCE TO RELATED APPLICATIONS

This application claims priority to U.S. Provisional Patent Application No. 62/259,007, filed on Nov. 23, 2015, titled "A Cloud-Based Radiation Therapy Treatment Planning System." The entire disclosure of Application No. 62/259,007 is hereby incorporated herein by reference.

STATEMENT REGARDING FEDERALLY SPONSORED RESEARCH

Not Applicable.

TECHNICAL FIELD OF THE INVENTION

The present disclosure relates generally to systems, methods, and apparatuses for radiation therapy treatment planning systems. More particularly, the disclosure relates to systems and methods for web-based radiation therapy treatment planning systems.

BACKGROUND

Curative radiation oncology treatment is designed to deliver a tumorcidal radiation dose to a cancerous target volume while simultaneously sparing healthy tissues. In order to achieve this, clinical personnel, treatment planning software, and radiation delivery hardware are leveraged to design and deliver a patient specific treatment course. Typically, computed tomography (CT) or magnetic resonance imaging (MRI) images are taken of the patient prior to or during treatment. These images are used to identify the tumor volume, normal healthy tissue, and healthy non-target organs and structures. The geometry of the treatment device together with the anatomical orientation of the patient, indicated by the image, is used to create a treatment plan.

Treatment planning is usually an iterative process that involves several clinicians. Typically, clinicians must manage treatment planning obligations within the scope of their other clinical duties. This creates a delay in communication between clinicians involved in the planning process. The communication delay in conjunction with computationally intensive treatment planning processes makes the entire treatment planning process exceedingly time consuming which can limit a clinic's patient throughput.

Recently, graphics processing units (GPU)s have been used to speed up treatment planning computation time. Since adequate computational GPU hardware is too large to be incorporated into mobile devices, conventional treatment planning systems are limited to a local stationary machine. The use of multiple GPU cards is also costly and large GPU servers are not practical for small clinics. If the computational power of a GPU server could be realized on a mobile device, the communication delay, and computational time would be dramatically reduced. This would not only enable clinics to treat patients more efficiently, it would also allow for higher quality treatment plans since computational shortcuts would not be required. Additionally, it would make online adaptive radiation therapy more clinically practical.

Thus, there is a need for a treatment planning computational framework that would allow for treatment planning on mobile devices. There also remains a need for server-based treatment planning systems.

SUMMARY

In view of the aforementioned problems and trends, embodiments of the present invention provide systems and methods for patient treatment planning.

According to an aspect of the invention, a treatment planning system includes a user device configured with a display; a remote computer server configured to link with the user device via a communication network, the server being configured to perform mathematical computations based on patient information communicated between the user device and the server via the network; and wherein the server is configured to determine a radiation dose calculation result for viewing on the user device display.

According to another aspect of the invention, a method for treatment planning includes linking a user device to a remote server via a communication network, the user device being configured with a display; communicating patient information between the user device and the remote server via the communication network; the remote server performing mathematical computations based on the communicated patient information to determine a radiation dose calculation result; and the remote server communicating the determined radiation dose calculation result for viewing on the user device display.

According to another aspect of the invention, a cloud-based treatment planning system includes a remote computer server configured to link with a user device via a communication network; the server having at least one processor configured to execute instructions to: perform mathematical computations based on patient information communicated between the user device and the server via the communication network; determine a radiation dose calculation result; and communicate the radiation dose calculation result for viewing on the user device.

Other aspects of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

DETAILED DESCRIPTION

Figure 1A:
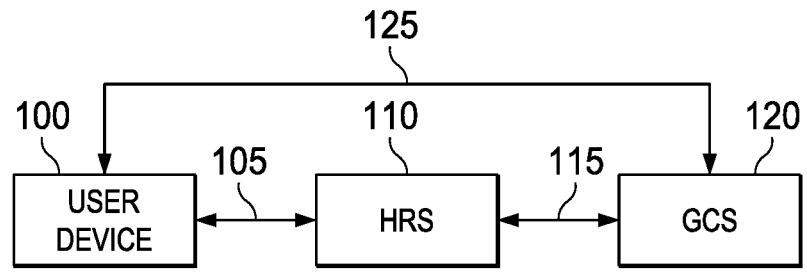
FIGS. 1a-1d depict four variants of a computer system architecture according to some embodiments of this disclosure.

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

Embodiments of this disclosure present radiation therapy treatment planning techniques. Embodiments of such treatment planning techniques may be implemented using conventional treatment planning software. For example, conventional dose calculation algorithms may be used to model the dose deposition of radiation in tissue, generated from the treatment device in a given delivery orientation. Common dose calculation algorithms used are ray tracing, finite sized pencil beam, collapsed cone convolution superposition, and Monte Carlo simulation. These algorithms take into account the patient's anatomy based on a 3-dimensional image of the patient, and the treatment delivery geometry of the radiation in a specific delivery orientation.

The vast majority of radiation therapy plans use external beam radiation therapy. In external beam radiation therapy, the dose calculation engines take into account the incident beam angle, the shape of the beam, and the angle of the couch supporting the patient, as well as the machine characteristics, to calculate a patient specific dose distribution. Due to the complex nature of the treatment delivery course, the dose calculation engine is often used in conjunction with an optimization engine. Embodiments of this disclosure cast treatment planning into an optimization routine allowing clinicians to generate radiation treatment plans inversely based on previously mentioned computational architecture. Inverse treatment planning includes the clinician specifying to the treatment planning system software the desired treatment result, tumor volume, critical structures, and various control parameters. The treatment planning algorithm can then generate the treatment based on the desired results and control variables. Clinicians may influence the underlying planning algorithms by modulating input control variables, such as but not limited to, adjusting critical structure weighting factors, specifying target dose volume histograms, or by using statistical analysis. Inverse treatment planning increases the quality of the treatment plan by allowing clinicians to specify a desired treatment result.

Commonly used inverse treatment planning strategies such as intensity modulated radiation therapy (IMRT) require large sets of treatment variables. The treatment variables are shifted iteratively, until the best possible solution is reached. IMRT is computationally intensive and can take upwards of ten minutes to complete. Usually, the treatment planning parameters are changed many times until an acceptable treatment plan is generated, which may take several hours.

Furthermore, the treatment planning workflow extends to more computationally expensive treatment strategies such as volumetrically modulated arc therapy, and adaptive radiation therapy. Embodiments of this disclosure entail a treatment planning computational framework that streamlines the processing steps and allows for mobile treatment planning.

In accordance with some embodiments, a framework for an entirely cloud-based radiation therapy treatment planning system (TPS) is disclosed. In some embodiments, a hardware framework broken up into two or three distinct computational components is present. The front-end user interface can be present on a browser such as INTERNET EXPLORER®, Google CHROME™, or Mozilla FIREFOX®. In accordance with some embodiments of this disclosure, on the server side one or more servers may utilize GPU hardware to facilitate ultra-fast physics computations. The treatment planning system can be divided into three computational components with a minimum of two components. In accordance with some embodiments, the TPS comprises a user's device, a hospital's relay server (HRS), and one or more external GPU cluster servers (GCS). The user's device handles simple computations capable of executing on lower performance processors such as graphic rendering and storing temporary patient information. In accordance with some embodiments of this disclosure, the HRS is located on the hospital's intranet and can thus have relatively fast network speeds. The HRS stores all patient data and can handle medium sized computations, such as automated organ contouring. The GPU hardware in the GCS can handle large, mathematically complex physics computations that run on high performance processors. In accordance with some embodiments, there are four variants to the current hardware infrastructure: 1. user's device, HRS, and GCS; 2. user's device and HRS only; 3. user's device, and GCS only; 4. or HRS and GCS only. Some disclosed embodiments provide a computational framework for concurrent and temporary storage of patient images and treatment planning information on the user's device and the GCS.

Some embodiments of the current disclosure provide a method for input of patient information including planning and contouring information on the user's device. In such embodiments, the information is concurrently sent and synchronized with the HRS and GCS servers.

Turning now to FIGS. 1a-1d, in accordance with some embodiments of this disclosure, four variants of the computer system architecture between the user, hospital's relay server (HRS) and the external GPU cluster server (GCS) are depicted. In FIG. 1a, a user device 100 connects through communication means 105 to one or more hospital relay servers (HRS) 110. In accordance with some embodiments, the user device 100 may be a handheld smartphone such as an Apple IPHONE®, Samsung GALAXY®, Motorola DROID™, Microsoft LUMIA® or a smartphone of similar functionality and performance. In other embodiments, the user device 100 may be a desktop computer, laptop computer or tablet device for use in a hospital, clinical environment, or outside the clinic. Communication means 105 connecting the user device 100 to the HRS 110 can be a local area network (LAN) intranet, wide area network (WAN), personal area network (PAN) such as Bluetooth network, wired Internet connection or wireless Internet connection. In some embodiments, user device 100 connects through communication means 125 to the GCS 120. Communication means 125 can be an Internet connection or a dedicated wired or wireless WAN connection in accordance with some embodiments of this disclosure. GCS 120 can be a multi-processor based Cluster server system with each multi-processor including multiple hardware cores or a GCS system. In accordance with some embodiments, communication means 115 connects and transfers information between HRS 110 and GCS 120. Communication means 115 can be an Internet connection or a dedicated wired or wireless WAN connection in accordance with some embodiments of the invention. HRS 110 can be desktop server computer systems or rack based server computer systems located on the hospital's intranet 105 with high network speeds (e.g., >100 Mbps).

Figure 1B:
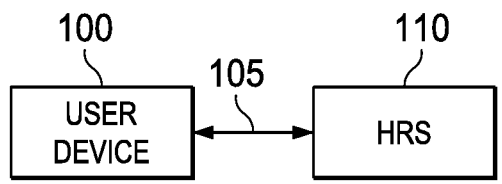

Turning now to FIG. 1b, in one embodiment, user device 100 connects through communication means 105 to one or more HRS 110. In accordance with some embodiments, the functionality and software implementation performed on the GCS 120 depicted in FIG. 1a and as described below is performed on the HRS 110.

Figure 1C:
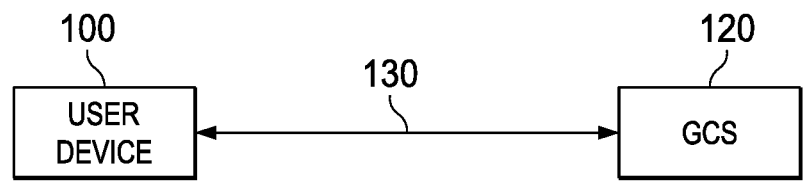

Turning now to FIG. 1c, user device 100 connects through communication means 130 to GCS 120. In accordance with some embodiments, the functionality and software implementation performed on the HRS 110 depicted in FIG. 1a and as described herein is performed on the GCS 120.

Figure 1D:
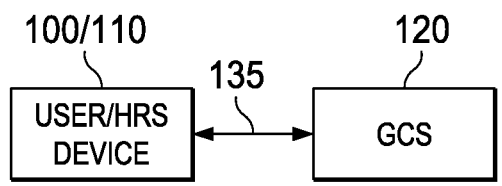

Turning now to FIG. 1d, user/HRS device 100/110 connects through communication means 135 to GCS 120. In some embodiments, a user may directly login to the hospital relay server 110 and connect to GCS 120. The functionality and software implementation performed on the User device 100 depicted in FIG. 1a and as described herein is performed on the HRS 110.

In accordance with embodiments described herein, the following is a description of the computer system architecture depicted in FIG. 1a. This disclosure does not limit the treatment planning system to the three computational components of FIG. 1a but also includes systems composed of two computational components, as depicted in FIGS. 1b-1d.

Figure 2:
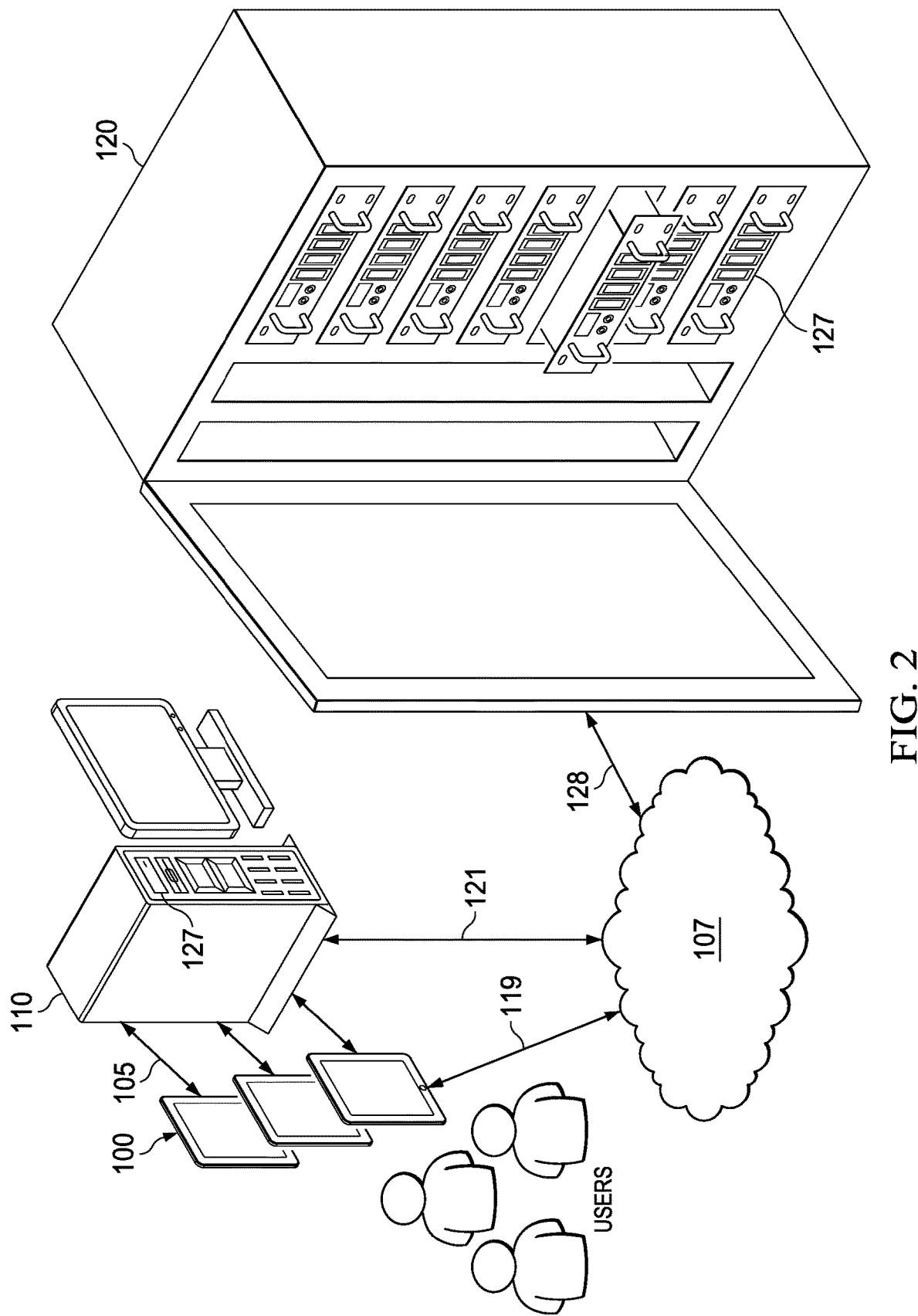
FIG. 2 depicts the computer system architecture of FIG. 1a for a treatment planning system according to an embodiment of this disclosure.

Referring to FIG. 2, a TPS 200 embodiment of this disclosure includes multiple users (via independent user devices 100) linked to HRS server node 110 through a high-speed communication network 105. Network 105 may be a local intranet network (e.g. within a hospital or clinic). In some embodiments, the user device(s) 100 may be linked to HRS server node 110 through the cloud 107 via Internet communication network 119. HRS node 110 is linked to the GCS 120 through the cloud 107 via Internet communication network 121. GCS 120 is linked into the cloud 107 via Internet communication network 128. It will be understood by those skilled in the art that the HRS 110 and GCS 120 servers of the embodiments disclosed herein may be implemented with state of the art microprocessors 127 and software configured to perform the functions disclosed herein.

In accordance with some embodiments, user device 100 handles, less intensive computations such as graphic rendering, simple physics computations, treatment planning input, and storing temporary patient information. When the HRS node 110 and the user device(s) 100 are linked into a hospital's intranet, relatively fast network speeds (e.g., >100 Mbps) are attainable. In some embodiments, the HRS 110 permanently stores all patient data and is responsible for medium sized computations requiring higher processing power. The GCS 120 interacts with the HRS 110 and stores patient planning information temporarily. The GCS 120 is responsible for heavy computations, such as dose calculation and treatment plan optimization. In some embodiments, the GCS 120 is a high performance, high throughput super-computer.

When a user opens a patient file via a user device 100, the HRS 110 communicates the patient information to the user's device 100 and to the GCS 120. In accordance with some embodiments, when the user enters planning information into the user's device 100, the information is simultaneously sent to the HRS 110 for permanent storage. The HRS 110 sends the planning information to the GCS 120 for temporary storage.

Once the user has entered all the planning information via the user device 100 and is ready to create a plan, in accordance with some embodiments, calculation of the plan occurs on the GCS 120. When the GCS 120 has finished calculating the plan, the results are first communicated to the user's device 100 through communication networks 125, 119 and then communicated to the HRS 110 through communication network 121, as depicted in FIG. 2.

In some embodiments, the TPS maintains privacy and confidentiality of image data and patient metadata by performing scrambling of the data using a user specific password generated each time the user logs into user device 100. The password is used to create a temporary index, which rearranges the data sent between the user device 100, HRS 110 and GCS 120 during the communication session. The patient information, prior to transmission, is stored in a buffer. The user device 100 scrambles the data in the buffer using the index and then transmits the data to HRS 110 and GCS 120. The HRS and/or GCS receive the data in the buffer and use the index to descramble the buffer. Similarly, whenever patient information is transferred between the user device 100, the HRS 110, or the GCS 120, the described scrambling technique may be implemented. This technique also provides an advantage of maintaining a constant buffer size, with a minimal increase of TPS complexity and computational overhead. In some embodiments, for added security, if patient information is transmitted outside of the hospital's secure intranet to the GCS 120, the information may be sent through the cloud 117 using a secure connection such as HTTPS, SSL, or TLS, with 256-bit encryption or other conventional encryption schemes. Information sent within the hospital's intranet may use the hospital's existing secure network.

Figure 3:
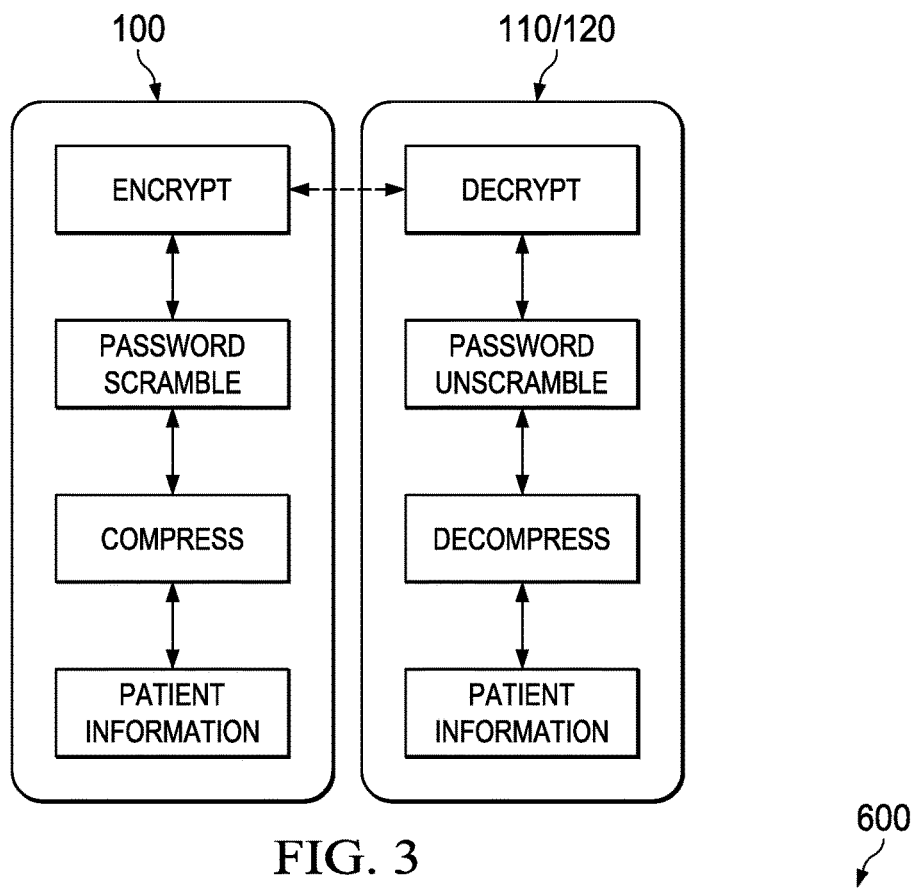
FIG. 3 depicts the communication of patient information between a user's device and a server according to some embodiments of this disclosure.

Turning now to FIG. 3, a communication protocol for an embodiment of this disclosure is depicted. In this embodiment, all patient information communicated between user device 100 and HRS 110 or GCS 120 is compressed using a lossless technique, scrambled as described above, and encrypted. The information is sent to the HRS 110 and/or GCS 120 server via a communication network as described herein. Upon receipt at the server, the information is decrypted, unscrambled as described above, and decompressed. Conventional data compression algorithms may be used to implement the embodiments. Encryption may also be implemented using a 256-bit encryption scheme or any other suitable data encryption technique. In some embodiments, the network speed and user's device 100 computational power are used to determine the optimal compression ratio for data transmission. The combined process (compressing, scrambling, encrypting/decompressing, descrambling, decrypting) of handling the communicated information provides a very secure mode of information exchange between the remote server (HRS 110 and/or GCS 120) and the user device 100.

In accordance with some embodiments, patient information including three-dimensional computed tomography (CT) information is sent in two-dimensional slices to the user device 100, starting with the central slice. Once the first slice loads onto the user's device 100, the user can start contouring or planning the treatment. By sending the CT image in this manner, the user can begin to work on the patient once the first slice arrives. If the clinic or hospital has a 100 Mbps upload speed, then a typical 512 by 512 CT image set with 133 slices using 256-bit encryption would take 44.63 seconds to transfer to the user. In accordance with embodiments of the invention, the first slice can be completely uploaded to the user's device in 0.042 seconds. Thus, the user can immediately start creating contours and planning treatment using the first slice. In accordance with some embodiments, the entire image can take 5.578 seconds to finish uploading, given a compression ratio of 8. The user device's 100 computation power and the user's network connection speed may be used to determine the optimal compression ratio for overall speed.

In some embodiments, once the user starts contouring and treatment planning, the user input to the user device 100 and data are continuously synchronized with the HRS 110 and GCS 120. Thus, every time the user completes an action or input to the user device 100, it is automatically sent to HRS 110 and/or GCS 120 without any user command or request. HRS 110 and/or GCS 120 computes the three-dimensional structure of each contour in a slice by slice fashion taking into account user inputs and treatment planning requests. As the user on device 100 is creating the plan, planning information is sent to HRS 110 and GCS 120 asynchronously in accordance with some embodiments. Thus, for example, when the user chooses an IMRT five field plan with given beam angles, HRS 110 or GCS 120 will automatically interpolate the data to determine the beam fluence map and associated dose once the tumor volume has been identified by the user. The radiation dose calculation result data is then communicated to the user device 100 for the user's viewing on the user device display. The user can then make modifications, if desired, to the plan by communicating new parameters via the user device 100 for recalculation and generation of a modified radiation dose calculation result.

By generating pre-planning information as the user enters data for the planning process, the TPS is able to skip computational steps after the user has completed data entry for the treatment planning process and is ready to start the treatment planning computation. This reduces the overall computational time of the treatment planning process. If the HRS 110 or GCS 120 is busy calculating another user's treatment plan, then the pre-planning computation is queued with low priority. When two users are attempting to calculate treatment plans near simultaneously and other users are creating treatment plans, the HRS 110 or GCS 120 will calculate the first user's treatment plan, queue computation of the second user's treatment plan with high priority and queue other user's pre-planning computations with lower priority.

In order to minimize the effect of network speed, contours of organs are sent between the HRS 110, GCS 120, and user device 100 in polygonised form as vertices in accordance with some embodiments. The contours may be transmitted slice by slice, each slice described by a polygon with a set of vertices. In such embodiments, the vertices for each slice are then used to reconstruct the volume of the contour as they are parsed and communicated to the user device 100. Depending on the computational power of user device 100, a mesh or a wire frame of the three-dimensional structure can be generated by combining each contour on the user's device 100. If the computational power of the user's device 100 can calculate a three-dimensional mesh, a conventional computer graphics algorithm (e.g. Marching Cubes algorithm) can be implemented on device 100 to generate the three dimensional meshes for the structure sets.

In accordance with some embodiments, for the TPS shown in FIGS. 1a-1b and FIG. 1d, HRS 110 stores all patient information on its hard drive. In the TPS shown in FIGS. 1a and FIGS. 1c-1d, GCS 120 permits temporary storage of patient information from multiple users. Once the user on user device 100 begins entering patient information, the necessary patient information is communicated to GCS 120 and is stored there temporarily. In accordance with some embodiments, results of GCS 120 computations are stored permanently on the hard drive of HRS 110 and also sent to the user device 100. The user's device 100 stores all information temporarily. All clinically relevant actions executed by user device 100 are automatically sent and stored permanently on the hard drive of the HRS 110. If the structure described in FIG. 1C is implemented, then the GCS 120 will store the patient information permanently.

During the treatment planning process, once the user on user device 100 has provided the treatment plan, target tumor volume, and organ contour information, the HRS 110 or GCS 120 will automatically calculate the optimal beam geometry and the resulting radiation dose.

In accordance with some embodiments, after the HRS 110 or GCS 120 has completed the treatment plan, the resulting dose volume histograms (DVH), and dose grid are communicated to user device 100. The radiation dose calculation result can then be viewed by the user on the device 100 display. The dose grid is indexed according to the patient's body volume and sent to the user device 100. The patient's body volume is used to un-index the radiation dose grid on the user device 100. Simultaneously, HRS 110 or GCS 120 can send emails and text messages to a list of recipients specified by the user, at any time or upon treatment plan completion. The emails and text messages can contain, notifications of treatment plan completion, contour completion, plan review requests, contour review requests, links to the patient's treatment plan results, or treatment plan results, depending on the user's preference.

Referring now to FIGS. 4a-4d, screen shots from the TPS software of test structures from slices of a patient's internal organs are depicted as viewed on a user device 100 display. FIGS. 4a-4d depict actual screen shots from embodiments as viewed on a browser interface displayed on a user device 100 (a desktop computer in this case). Via the user device 100, a user may input patient identification information (e.g., name or coded number) to access the patient's medical files and related information. Once a patient's file is opened, images of the patient's organ structures of interest can be viewed. The CT or MRI images of the organ structures can be viewed in slices (left side images of FIGS. 4a-4d) and in 3D mesh form (right side images of FIGS. 4a-4d).

Figure 4A:
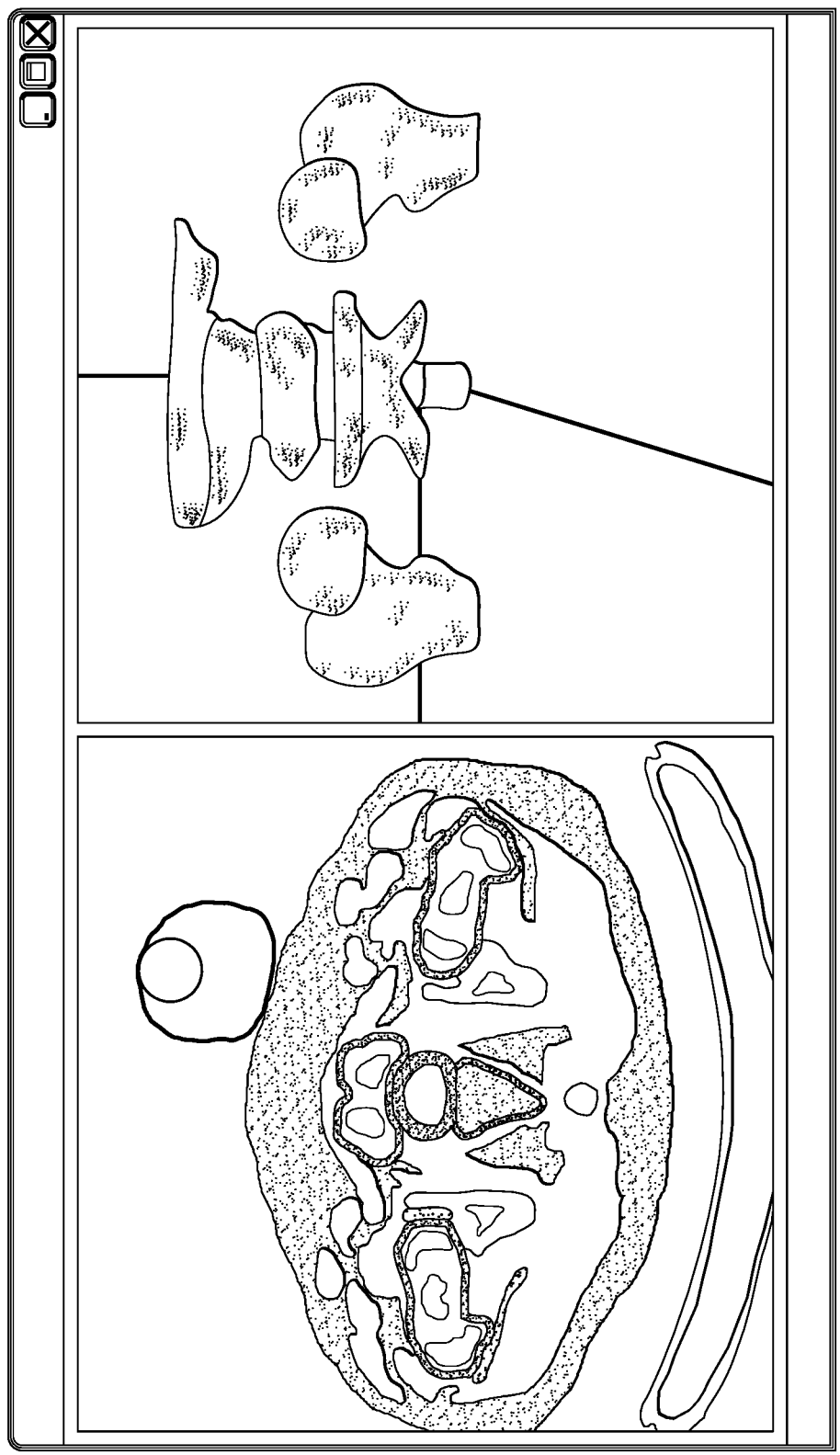
FIGS. 4a-4d depict screen shots (as viewed on a browser) from the TPS software of test structures from slices of a patient's internal organs according to some embodiments of this disclosure.
Figure 4B:
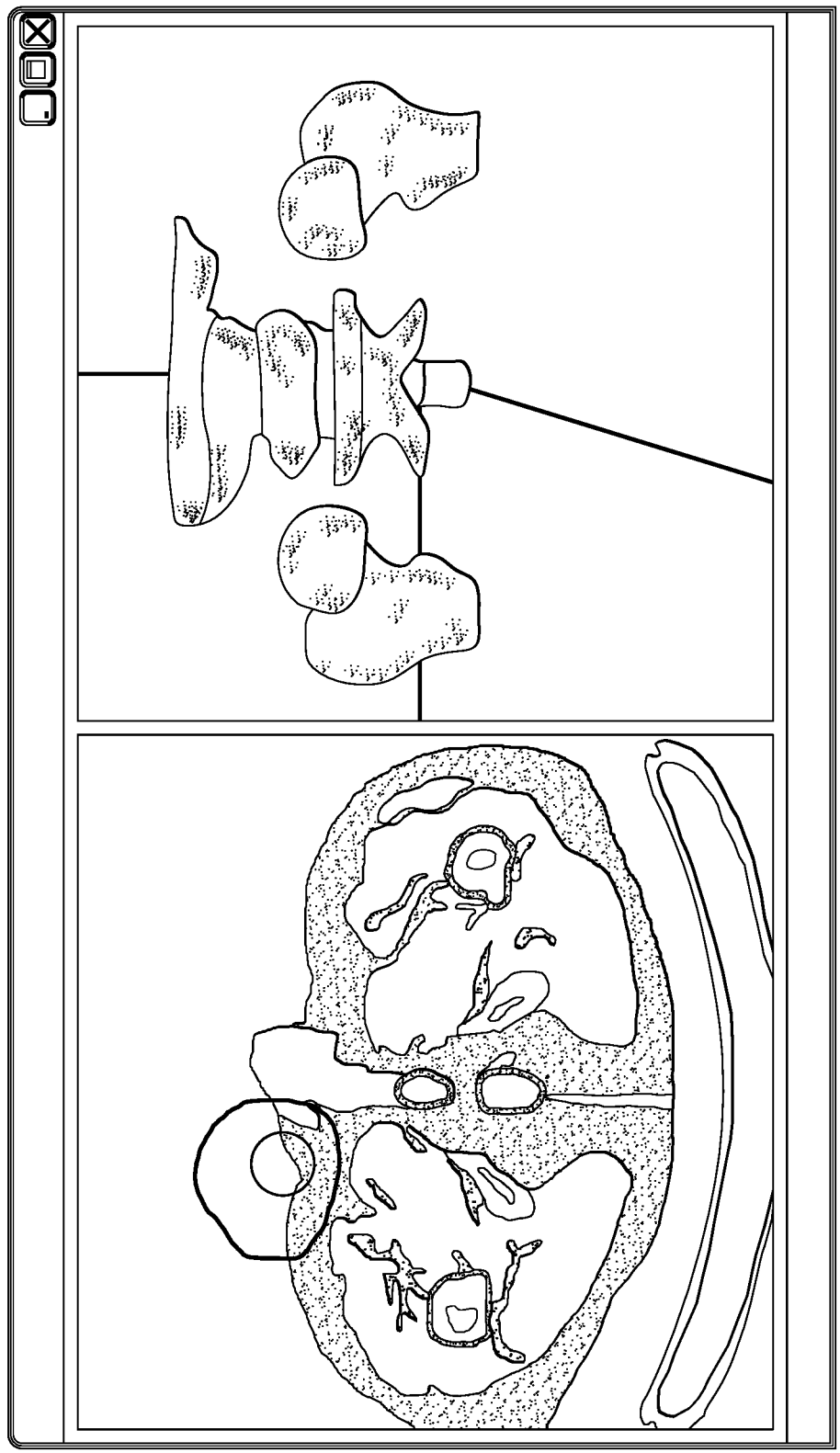
Figure 4C:
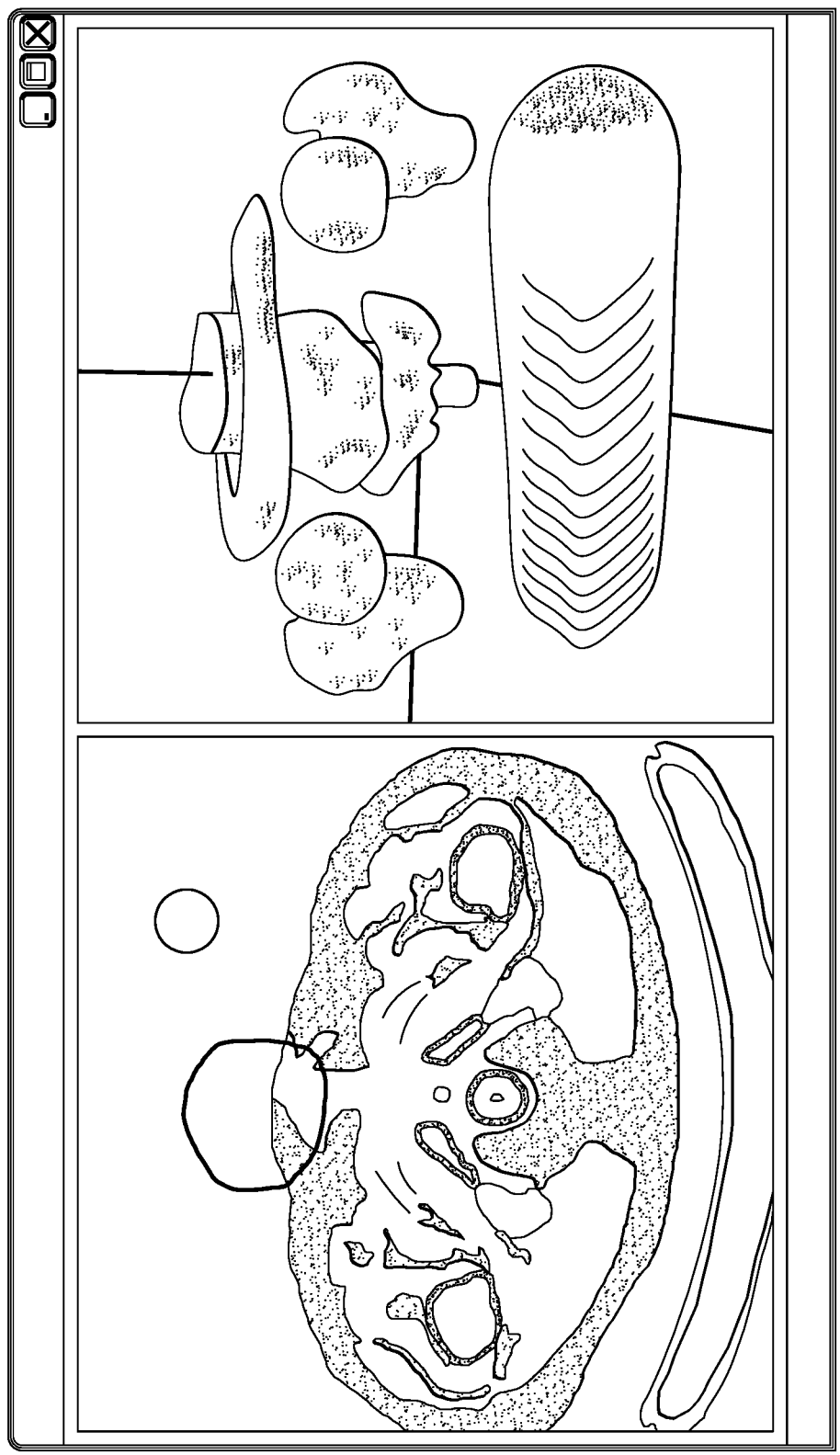
Figure 4D:
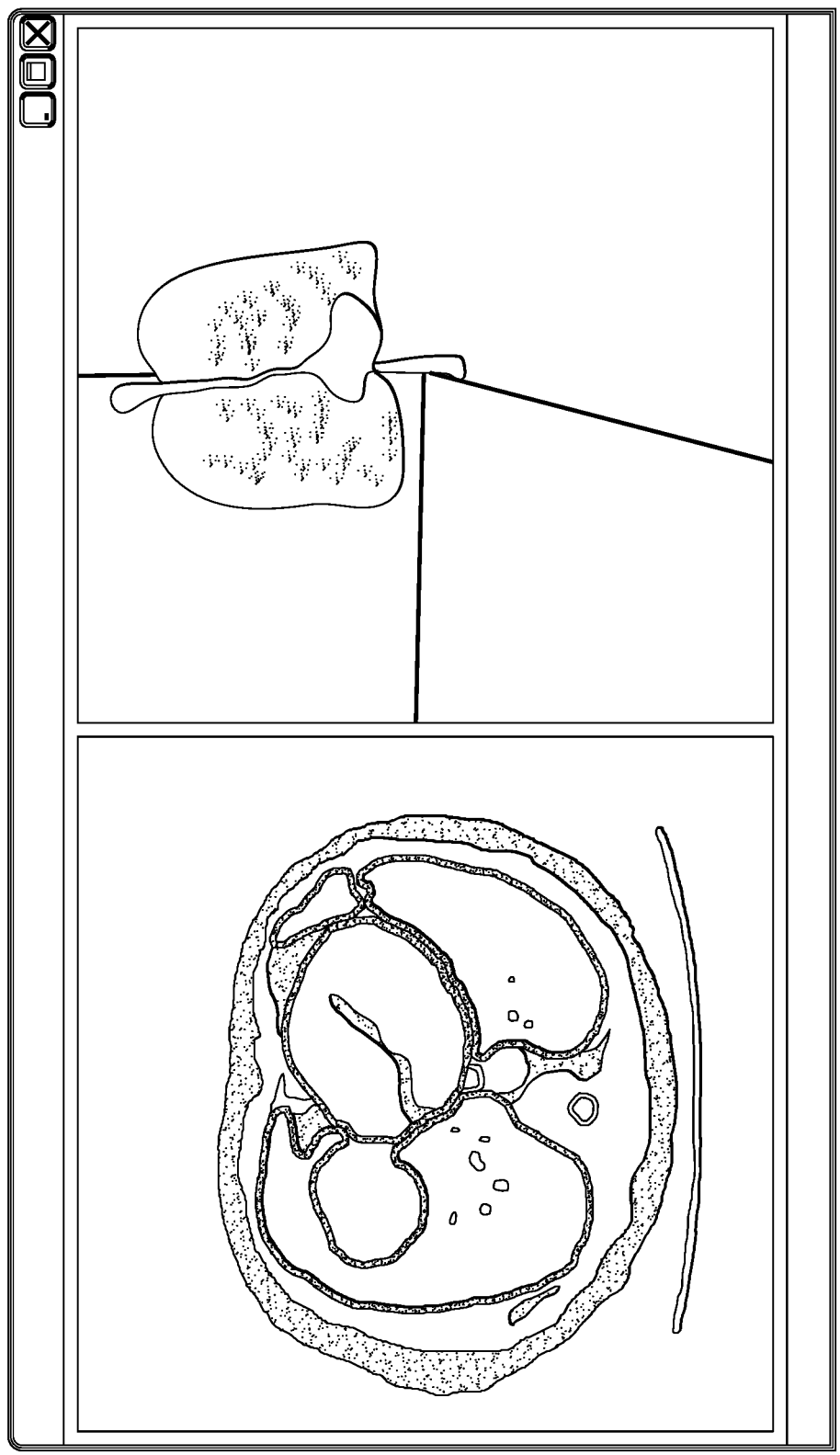

The user can scroll through the images of the organ structure slices to define a tumor volume and location by drawing the tumor starting/ending positions and defining the shape within the structure. FIG. 4a depicts the starting point of a test structure as drawn on the $21^{st}$ axial slice of a prostate patient. FIG. 4b depicts the ending point of the test structure as drawn on the $6^{th}$ slice. The server (HRS 110 and/or GCS 120) performs the calculations, interpolating the defined tumor volume within the imaged organ structure of the patient. FIG. 4c depicts the interpolated test structure at slice 11, with its associated 3D mesh depicted on the right side of the image. A user can work on treatment plans for multiple patients by switching between patient files viewed on the user device 100 display. FIG. 4d depicts a lung patient's data being opened simultaneously in a user device 100 browser. The user can view and modify the defined tumor structure and save the files as desired.

Figure 5A:
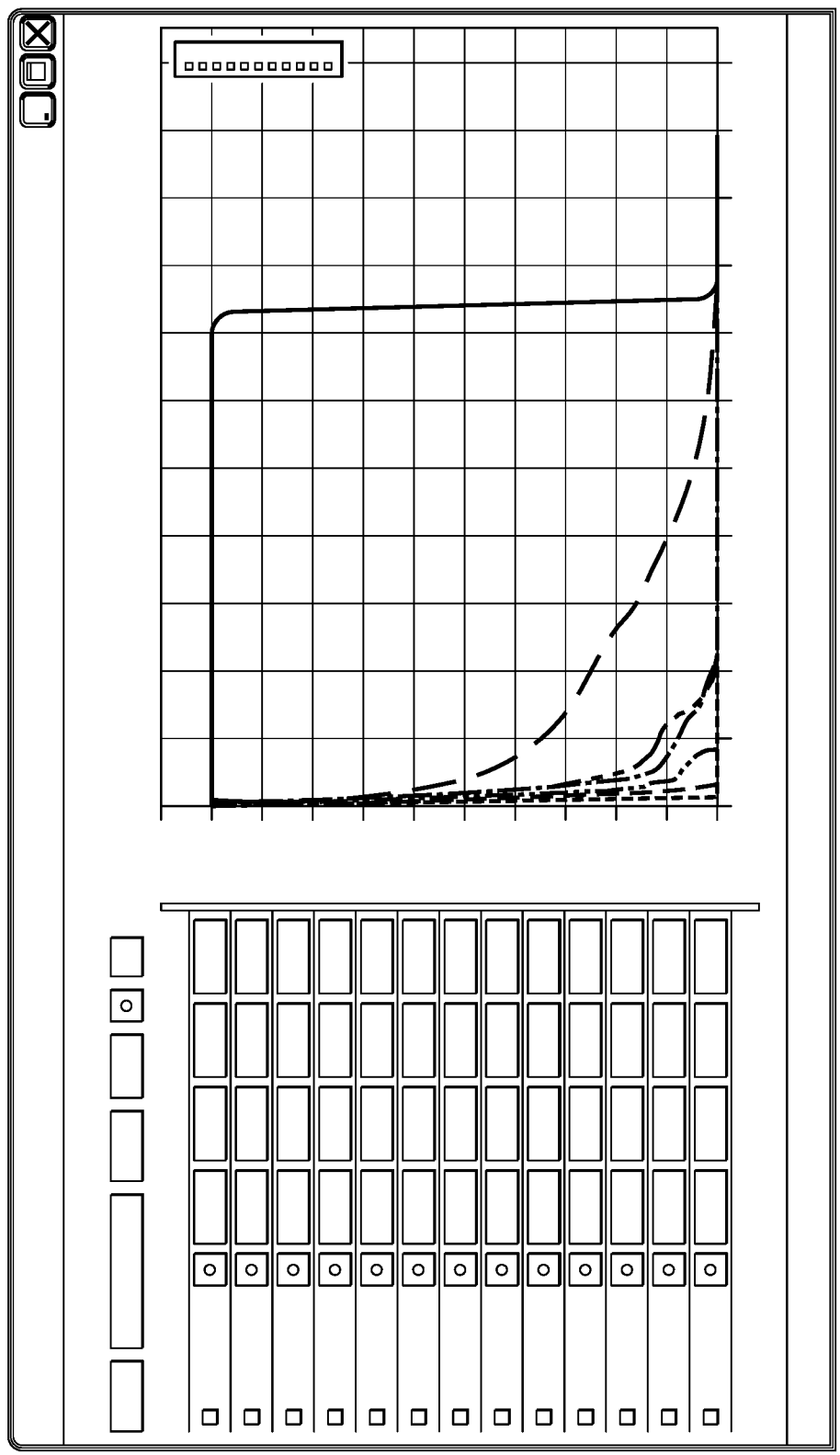
FIGS. 5a-5d depict screen shots (as viewed on a browser) of the workflow of a treatment planning process according to some embodiments of this disclosure.
Figure 5B:
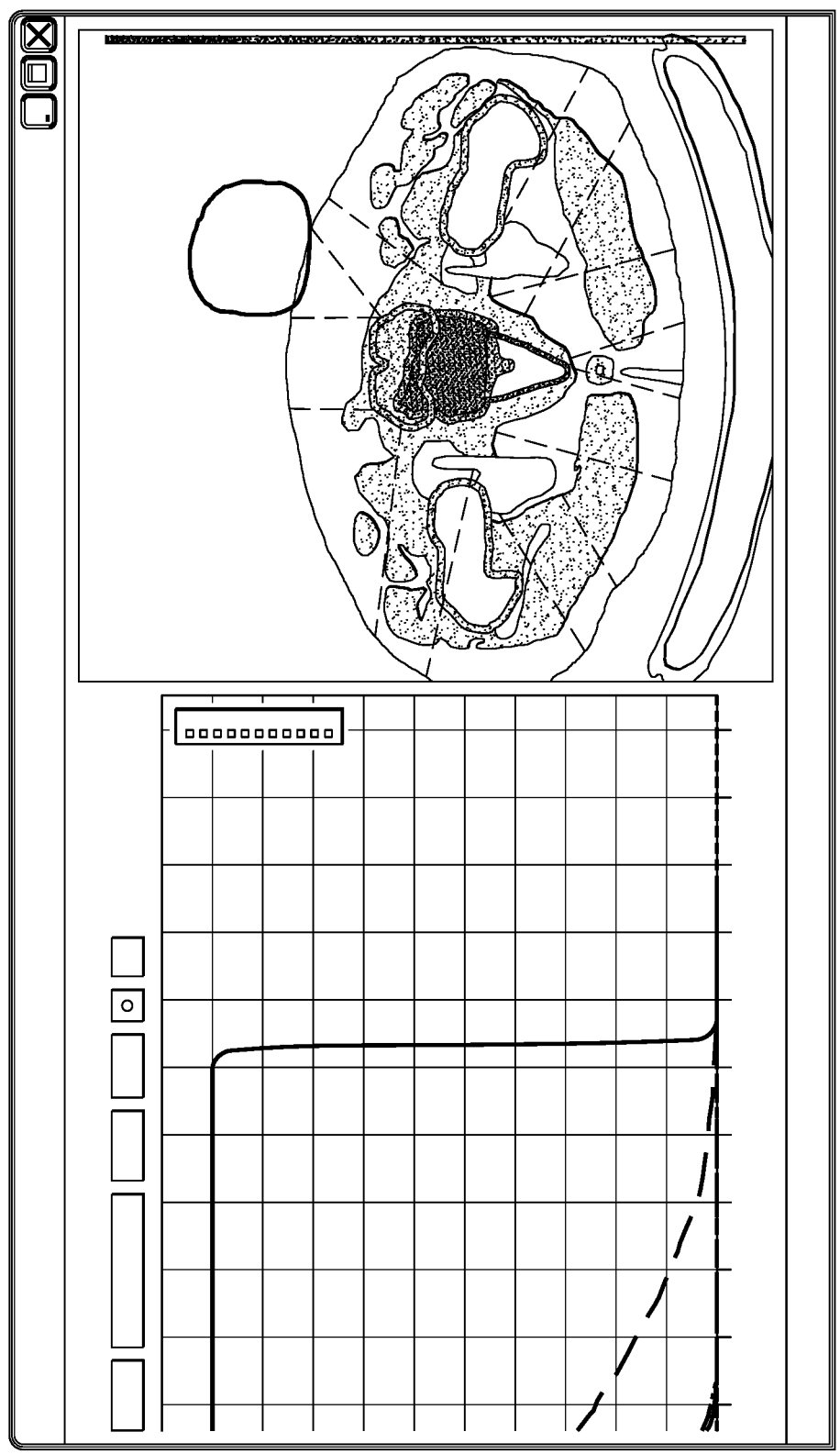
Figure 5C:
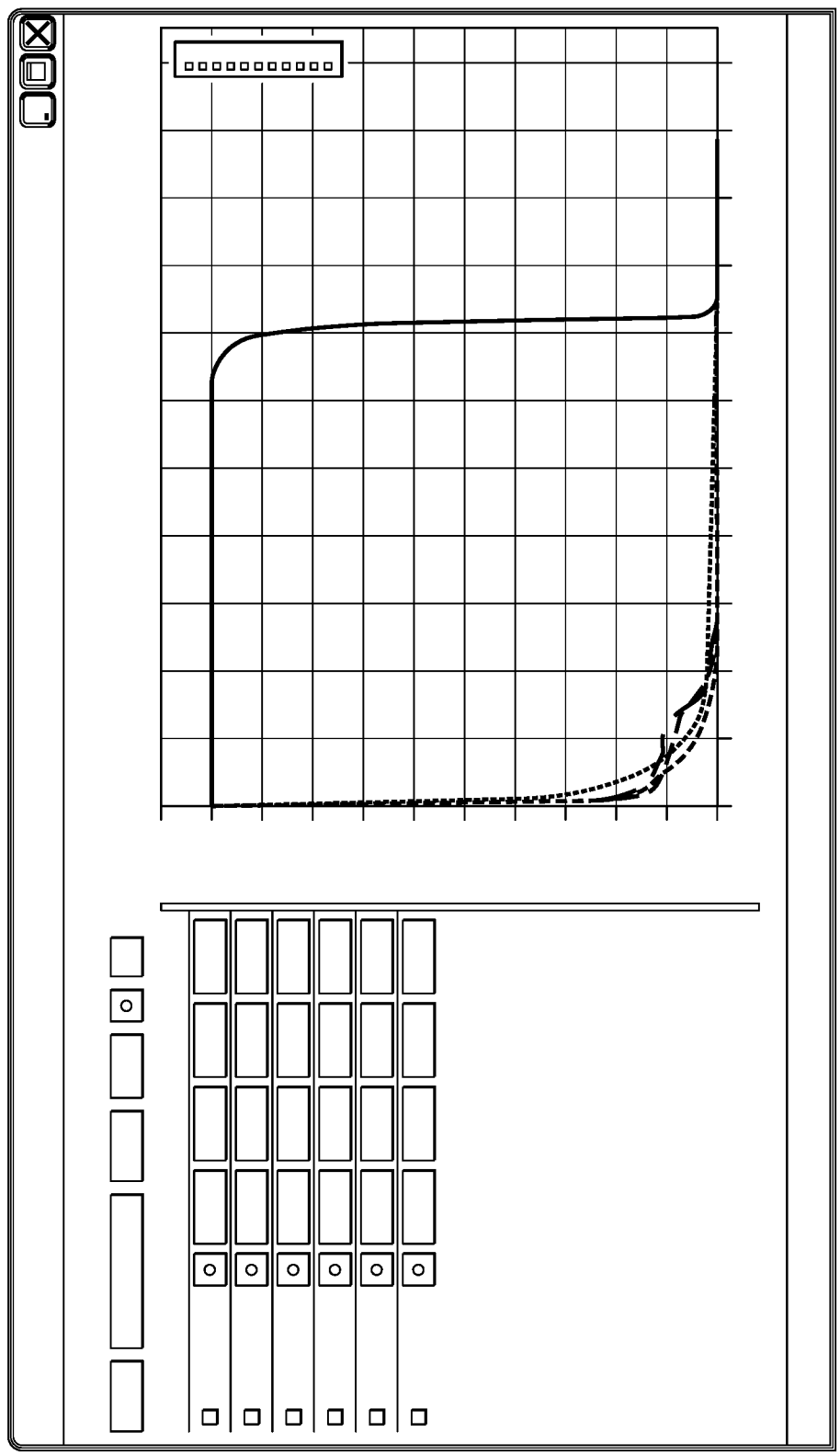
Figure 5D:
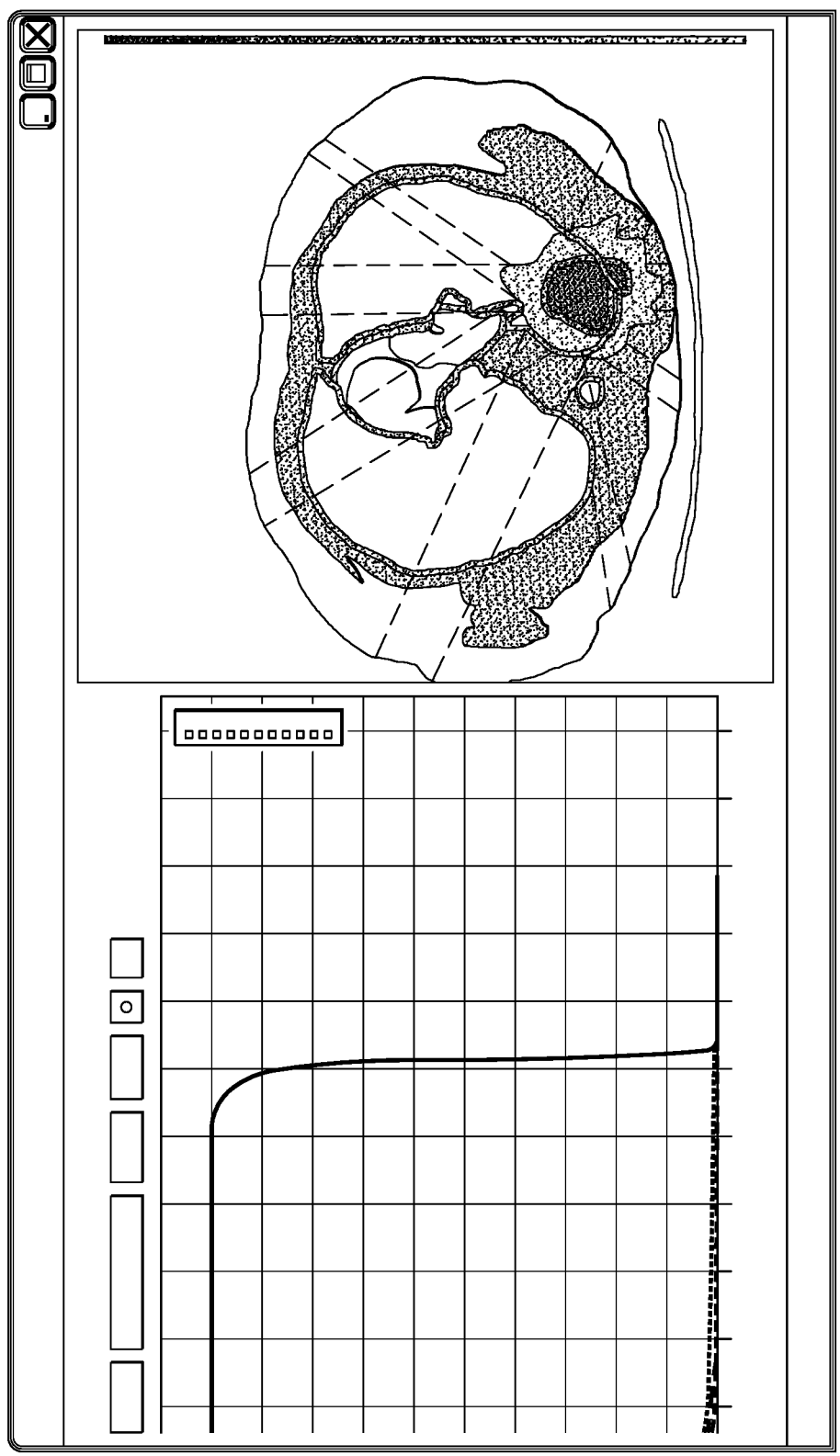

Once the user is satisfied with the defined structure, the user can commence the planning session to create an IMRT treatment plan via the user device 100. FIGS. 5a-5d depict a planning session workflow of the TPS. FIGS. 5a-5d depict actual screen shots from embodiments as viewed on a browser interface displayed on a user device 100 (a desktop computer in this case). The user inputs the patient information for the desired treatment plan (e.g., setting a radiation maximum or minimum parameter, range, and penalties for the target volume or organs at risk). The various patient treatment planning information and parameters that can be input for computation will be understood by those skilled in the art. FIG. 5a depicts the treatment planning conditions and the dose value histograms (DVH) result computed by the server (HRS 110 and/or GCS 120) from the treatment planning information provided for a prostate patient. The table on the left-hand side of FIG. 5a depicts the various fields for information entry by the user. FIG. 5b depicts the radiation dose grid computed by the server (HRS 110 and/or GCS 120) from the optimization result for the prostate patient of FIG. 5a. Once the radiation dose calculation result is displayed, the user can revise the plan by modifying the optimization parameter fields for a re-calculation if desired. FIG. 5c depicts a lung patient being worked on simultaneously and provides the treatment planning conditions and the DVH result from the optimization for the lung patient. FIG. 5d depicts the calculated dose grid from the optimization result for the lung patient of FIG. 5c.

Figure 6:
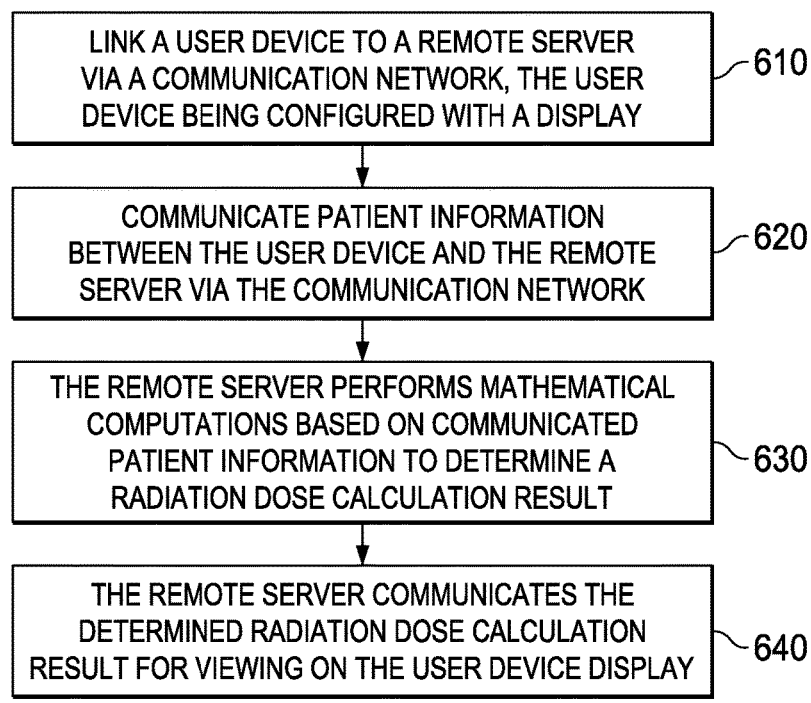
FIG. 6 is a flow chart depicting, at a top level, a method for treatment planning, according to some embodiments of this disclosure.

FIG. 6 is a flow chart depicting a method 600 according to an embodiment of this disclosure, i.e., a method for treatment planning. At step 610, a user device is linked to a remote server via a communication network, the user device being configured with a display. The user device and the server may be any of the devices as disclosed herein. The communication network may be implemented via any of the disclosed communication means. In step 620, patient information is communicated between the user device and the remote server via the communication network. In step 630, the remote server performs mathematical computations based on the communicated patient information to determine a radiation dose calculation result. The mathematical computations may entail any of the processing steps and algorithms disclosed herein. At step 640, the remote server communicates the determined radiation dose calculation result for viewing on the user device display. FIGS. 4a-4d and 5a-5d depict sample patient information entries and calculation results as viewed on a user device display in accordance with embodiments disclosed herein. This method 600 can be practiced by implementation of any of the embodiments disclosed and described herein.

In light of the principles and example embodiments described and depicted herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered. This disclosure describes one or more embodiments wherein various operations are performed by certain systems, applications, modules, components, etc. In alternative embodiments, however, those operations could be performed by different components. Also, items such as applications, modules, components, etc., may be implemented as software constructs stored in a machine accessible storage medium, such as an optical disk, a hard disk drive, etc., and those constructs may take the form of applications, programs, subroutines, instructions, objects, methods, classes, or any other suitable form of control logic; such items may also be implemented as firmware or hardware, or as any combination of software, firmware and hardware, or any combination of any two of software, firmware and hardware. The term "processor" may refer to one or more processors.

This disclosure may include descriptions of various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A method for planning radiation treatment, the method comprising:
    (a) a user opening a file for a patient on a user device;
    (b) a local server that stores three-dimensional imaging data and is connected to the user device and a remote server via a network transmitting to the user device a two-dimensional image slice of the three-dimensional imaging data;
    (c) the user reviewing the two-dimensional image slice received with the user device and inputting tissue contours for patient tissue visible in the two-dimensional image slice;
    (d) the user device automatically transmitting the tissue contours as they are input by the user to the remote server;
    (e) the remote server using the tissue contours to compute a three-dimensional structure for the tissue contour;
    (f) repeating steps (b)-(e) until three-dimensional structures have been computed by the remote server for each input tissue contour for each two-dimensional image slice;
    (g) the remote server calculating an optimal beam geometry and resulting radiation dose based upon the calculated three-dimensional structures; and
    (h) the remote server transmitting the calculated optimal beam geometry and resulting radiation dose to the user device.

2. The method of claim 1, wherein the user device is a desktop computer or a laptop computer.

3. The method of claim 1, wherein the user device is a handheld smartphone or a tablet device.

4. The method of claim 1, wherein the three-dimensional imaging data comprises computed tomography (CT) data or magnetic resonance imaging (MRI) data.

5. The method of claim 1, wherein transmitting the tissue contours comprises transmitting the tissue contours in polygonised form as vertices.

6. The method of claim 1, further comprising the user selecting a treatment plan on the user device and the user device automatically transmitting the selected treatment plan to the remote server.

7. The method of claim 6, wherein the treatment plan is an intensity modulated radiation therapy (IMRT) five-field treatment plan.

8. The method of claim 1, further comprising the user inputting a tumor volume on the user device and the user device automatically transmitting the tumor volume to the remote server.

9. The method of claim 1, wherein the remote server further calculates dose volume histograms and a dose grid and transmits them to the user device.

10. The method of claim 9, further comprising the user device displaying the dose volume histograms and the dose grid to the user.

11. The method of claim 9, wherein the dose grid is indexed according to a body volume of the patient, and the body volume is used to un-index the radiation dose grid on the user device.

12. The method of claim 9, wherein the remote server is configured to send a notification regarding the treatment plan.

13. The method of claim 12, wherein the notification regarding the treatment plan is at least one of: notification of treatment plan completion, notification of contour completion, plan review request, contour review request, treatment plan results, and a link to treatment plan results.

14. The method of claim 1, further comprising a second user reviewing a two-dimensional image slice received with a second user device and also inputting tissue contours to be used by the remote server to calculate the optimal beam geometry and resulting radiation dose.

15. A system for planning radiation treatment, the system comprising:
    a local server that stores three-dimensional imaging data for a patient;
    a remote server comprising a graphics processing unit; and
    a user device connected to the local server and the remote server via one or more networks, the user device being configured to receive the three-dimensional imaging data from the local server one two-dimensional image slice at a time, the user device further being configured to receive tissue contours input by a user for patient tissue visible in the two-dimensional image slices, the user device further being configured to automatically transmit the tissue contours to the remote server as they are input by the user;
    wherein the remote server is configured to receive the three-dimensional imaging data from the local server and the tissue contours from the user device and compute a three-dimensional structure for each tissue contour of each two-dimensional image slice, the remote server further being configured to calculate an optimal beam geometry and resulting radiation dose based upon the calculated three-dimensional structures.

16. The system of claim 12, wherein the user device is a desktop computer or a laptop computer.

17. The system of claim 12, wherein the user device is a handheld smartphone or a tablet device.

18. The system of claim 12, wherein the user device is configured to transmit the tissue contours in polygonised form as vertices.

19. The system of claim 12, wherein the user device is further configured to receive selection of a treatment plan input by the user and automatically transmit the selected treatment plan to the remote server.

20. The system of claim 12, wherein the user device is further configured to receive a tumor volume input by the user and automatically transmit the tumor volume to the remote server.

21. The system of claim 12, wherein the remote server is further configured to calculate dose volume histograms and a dose grid and transmit them to the user device.

22. The system of claim 18, wherein the user device is configured to display the dose volume histograms and the dose grid to the user.

23. The system of claim 21, wherein the dose grid is indexed according to a body volume of the patient, and the body volume is used to un-index the radiation dose grid on the user device.

24. The system of claim 21, wherein the remote server is configured to send a notification regarding the treatment plan.

25. The system of claim 24, wherein the notification regarding the treatment plan is at least one of: notification of treatment plan completion, notification of contour completion, plan review request, contour review request, treatment plan results, and a link to treatment plan results.

26. The system of claim 12, further comprising a second user device also configured to receive the three-dimensional imaging data from the local server one two-dimensional image slice at a time, receive tissue contours input by a second user for patient tissue visible in the two-dimensional image slices, and automatically transmit the tissue contours to the remote server as they are input by the second user.

* * * * *